(12) United States Patent
Leong et al.

(10) Patent No.: US 7,525,649 B1
(45) Date of Patent: Apr. 28, 2009

(54) SURFACE INSPECTION SYSTEM USING LASER LINE ILLUMINATION WITH TWO DIMENSIONAL IMAGING

(75) Inventors: Jenn-Kuen Leong, San Jose, CA (US); Guoheng Zhao, Milpitas, CA (US); Mehdi Vaez-Iravani, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/875,240

(22) Filed: Oct. 19, 2007

(51) Int. Cl.
*G01N 21/00* (2006.01)
(52) U.S. Cl. .................................. 356/237.1; 356/237.6
(58) Field of Classification Search .............. 356/237.1, 356/237.2, 237.6, 445
See application file for complete search history.

(56) References Cited

U.S. PATENT DOCUMENTS 6,608,676 B1 * 8/2003 Zhao et al. ............... 356/237.2

6,724,473 B2 4/2004 Leong et al.

OTHER PUBLICATIONS

Stokowski et al., "Wafer Inspection Technology Challenges for ULSI Manufacturing," International Conference on Characterization and Metrology for ULSI Technology, Mar. 1998, 11 pages.

* cited by examiner

*Primary Examiner*—Roy M Punnoose
(74) *Attorney, Agent, or Firm*—Kevin L. Daffer; Daffer McDaniel, LLP

(57) ABSTRACT

A surface inspection apparatus and a method are provided which include an illumination system configured to focus a beam of radiation at a non-orthogonal incidence angle to form an illumination line on a surface substantially in a plane of incidence of the focused beam. The apparatus and method further include a collection system configured to image the illumination line onto an array of detectors oriented parallel to the illumination line. The collection system includes an imaging lens for collecting light scattered from the illumination line, a focusing lens for focusing the collected light, and the array of detectors, each configured to detect a corresponding portion of the illumination line. The collection system may be configured to image the illumination line such that the width of the imaged illumination line on the array of detectors is larger than the pixel size of the detectors along the same direction.

19 Claims, 3 Drawing Sheets

SURFACE INSPECTION SYSTEM USING LASER LINE ILLUMINATION WITH TWO DIMENSIONAL IMAGING

BACKGROUND OF THE INVENTION

1. Field of the Invention

This invention generally relates to surface inspection systems and, more specifically, to an apparatus and method for inspecting a surface using line-illumination imaging techniques.

2. Description of the Related Art

The need to inspect surfaces of objects is prevalent in many situations and for a variety of purposes. For example, it is generally advantageous to inspect surfaces of semiconductor wafers for defects and/or examination of features. Some surface inspection tools employ systems for illuminating a region of a surface, such as a semiconductor wafer. In some systems, the illumination beam may be specifically configured to illuminate a line-shaped region of the surface to be inspected. In such cases, the surface inspection system may further include systems, such as charge coupled devices, for imaging the illuminated line using light sensitive elements (referred to herein as detector elements) to collect photons from the illuminated line. After given period of time, the electrons generated from the photons are converted to a voltage and the measured voltage is passed through an analog-to-digital converter to form a digital image.

In some embodiments, a width of an image of an illumination line on a CCD may be narrower than the pixel size of a detector element along a direction perpendicular to the illuminated line (referred to herein as the "x-direction"), assuming the detector elements are oriented parallel to the illuminated line. A consequence of such a scenario is that the optical resolution of the image along the x-direction is dependent upon the width of the illumination line on the surface being inspected rather than the optical spot size of the collection system. Such a state of affairs may be referred to herein as "one-dimensional (1-D) imaging" since only one dimension (i.e., the dimension parallel to illuminated line, referred to herein as the "y-direction") of the image is dependent upon the optical spot size of the collection system.

For the reasons noted above, the width of an illumination line may affect the sensitivity of a surface inspection tool in the x-direction and optical spot size of the collection system may affect the sensitivity of the tool in the y-direction. Objects which may be particularly susceptible to surface inspection tool sensitivity are semiconductor wafers. In particular, as feature sizes of semiconductor wafers continue to shrink, more stringent requirements on the sensitivity of wafer inspection instruments are typically imposed. In order to detect relatively small defects and/or features, it may be desirable to minimize the optical spot size of a collection system (to increase sensitivity of a tool in the y-direction) and/or minimize the width of an illumination line on surfaces to be inspected (to increase sensitivity of the tool in the x-direction).

In some cases, however, the width of an illumination line may be limited by the capabilities of the surface inspection tool. For example, some surface inspection tools (e.g., a tool using a 266 nm or greater wavelength laser) are not capable of illuminating lines having width dimensions less than 1.0 micrometer. In order to obviate such a limitation, it would be advantageous to develop a surface inspection system which is configured to image an illuminated line which is independent of the width of the illumination line. In other words, it would be beneficial to develop a surface inspection system based upon two dimensional imaging. In this manner, sensitivity of the surface inspection system in both the x and y directions may be dependent on the optical resolution of the collection system and increasing the sensitivity may be accomplished by reducing the optical spot size of its collection system.

SUMMARY OF THE INVENTION

The problems outlined above may be in large part addressed by an apparatus and a method for inspecting a surface. The following are mere exemplary embodiments of the apparatus and method and are not to be construed in any way to limit the subject matter of the claims.

Embodiments of the surface inspection apparatus and method include an illumination system configured to focus a beam of radiation at a non-orthogonal incidence angle to form an illumination line on the surface substantially in a plane of incidence of the focused beam. The apparatus and method further include a collection system configured to image the illumination line onto an array of detectors oriented parallel to the illuminated line. The collection system includes an imaging lens for collecting light scattered from the illumination line, a focusing lens for focusing the collected light, and an array of detectors, each configured to detect a corresponding portion of the magnified image. In some cases, the collection system is configured to image the illumination line in a manner such that the width of the imaged illumination line on the array of detectors is larger than the pixel size of the detectors along the same direction. In some embodiments, the collection system includes a plate with a narrow slit interposed between the focusing lens and the array of detectors.

BRIEF DESCRIPTION OF THE DRAWINGS

Other objects and advantages of the invention will become apparent upon reading the following detailed description and upon reference to the accompanying drawings in which.

Figure 1:
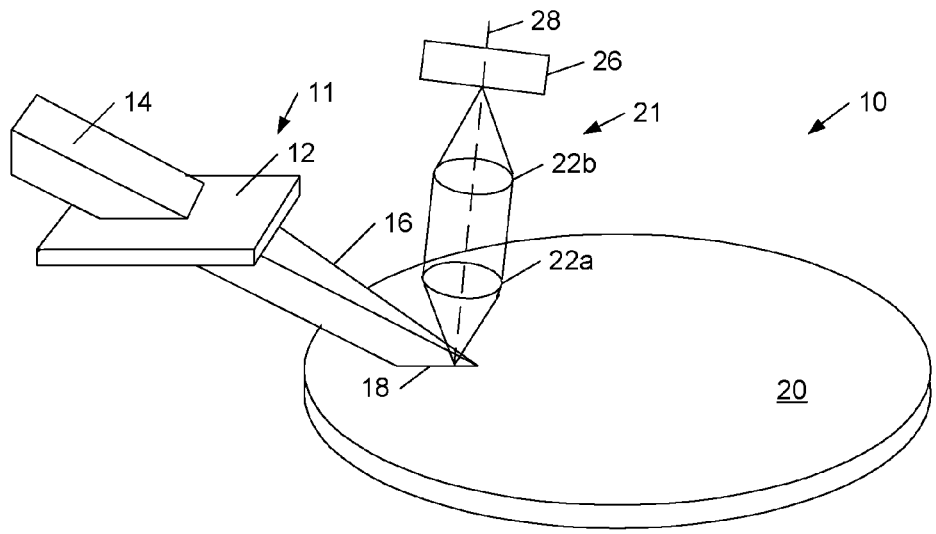
FIG. 1 depicts a perspective view of a surface inspection system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Turning now to the drawings, exemplary embodiments of surface inspection systems and methods for imaging illuminated lines on surfaces using such systems are illustrated. In particular, FIG. 1 depicts a perspective view of surface inspection apparatus 10 having illumination system 11 and collection system 21 for inspecting areas of surface 20. In addition, FIGS. 2-4 respectively illustrate partial cross-sectional views of surface inspection systems 30, 40 and 50 having alternative configurations of collections systems as compared to apparatus 10. Furthermore, FIG. 5 illustrates a flowchart of a method for imaging areas of surfaces using the systems described in reference to FIGS. 1-4 as well as the systems described herein having variations to the systems depicted in FIGS. 1-4.

In general, the surface inspection systems described herein may be used to inspect a surface of any object. For example, the systems may be used to inspect rough films, patterned or unpatterned semiconductor wafers, solar cells, backsides of wafers, as well as photomasks, reticles, liquid crystal displays or other flat panel displays. In addition to detection of anomalies within surfaces, the apparatuses described herein may also be used to detect other features such as markers or device structures. Although the description provided herein is specifically directed to inspection of semiconductor wafers, the use of surface inspection systems provided herein is not necessarily so limited. As such, surface 20 is not necessarily restricted to its illustration in FIG. 1. It is noted, surface inspection apparatus 10 and all other surface inspection apparatuses described herein are robust and tolerant of height variations and tilt of the surfaces they are configured to inspect. Furthermore, the surface inspection apparatuses described herein may, in some embodiments, include support structures for the surfaces they are configured to inspect.

As noted above, surface inspection apparatus 10 in FIG. 1 includes illumination system 11 and collection system 21 for inspecting areas of surface 20. As shown in FIG. 1, illumination system 11 is configured to direct light beam 14 through lens 12. Light beam 14 may be created by any appropriate light source known in the art such as a laser and, in some embodiments, may be collimated. In general, light beam 14 and lens 12 are configured such that focused beam 16 illuminates an area of surface 20 in the shape of illumination line 18. More specifically, lens 12 is oriented so that its principal plane is substantially parallel to surface 20 and, as a result, illumination line 18 is formed on surface 20 in the focal plane of lens 12. In addition, light beam 14 and, consequently, focused beam 16 are directed at a non-orthogonal angle of incidence to surface 20. In particular, light beam 14 and focused beam 16 may be directed at an angle between about 1 degree and about 85 degrees from a normal direction to surface 20. In this manner, illumination line 18 is substantially in the plane of incidence of focused beam 16. The incidence plane of focused beam 16 is defined by the common plane containing the direction of light beam 14 and the direction that is normal to surface 20. The formation of illumination line 18 in the aforementioned manner is noted in block 60 of the flowchart depicted in FIG. 5.

Regardless of the manner illumination line 18 is produced, the size of light beam 14 and the physical aperture of lens 12 affect the size of illumination line 18 and, therefore, light beam 14 and/or lens 12 may, in some embodiments, be configured to optimize the size of the illumination line. In particular, an optional expander may, in some embodiments, be placed along light beam 14 to govern the length of illumination line 18. In addition or alternatively, lens 12 may include multiple lenses for tighter focusing of light beam 14 and, in effect, produce a relatively narrow illumination line on surface 20. In other embodiments, lens 12 may include a single lens. In yet other cases, lens 12 may include cylindrical mirrors. Exemplary ranges of widths and lengths for illumination line 18 may be between approximately 1.0 micrometer and approximately 10 micrometers and between approximately 0.5 millimeters and approximately 20 millimeters, respectively. Larger or smaller widths and/or lengths, however, may be generated, depending on the wavelengths of light the light sources of the tool are configured to emit.

In some cases, it may be desirable to minimize the width of an illuminated line in order to achieve high sensitivity. A narrow illumination line also minimizes focus variation along the y-direction of a detector for two-dimensional imaging. For example, it may be desirable to minimize the width of an illumination line to approximately 1.0 micrometer or less for system that includes a 266 nm wavelength light source. In contrast, it may be advantageous, in some embodiments, to maximize the width of an illumination line. In particular, as the width of an illuminated line is reduced, throughput is generally reduced. More specifically, more time is needed to scan a surface since the illuminated line is narrower. In addition, a narrower illumination line imposes a much more stringent requirement for alignment and registration. In any case, it may be desirable in some embodiments to configure illumination line 18 to have a relatively long length, such as approximately 10 millimeters for example, in order to avoid the variation of intensity along the line.

As noted above, surface inspection apparatus 10 includes collection system 21 for imaging illumination line 18. More specifically, collection system 21 includes lens 22a for collecting light scattered from illumination line 18 and lens 22b for focusing the light coming out of lens 22a onto a device, such as charge coupled device (CCD) 26, comprising an array of light sensitive detectors. The light sensitive detectors of CCD 26 may sometimes be referred to herein as detector pixels. Such a term is not to be confused with the term image pixel, which is generally defined as a distinct element of a plurality of elements constituting an image. In some embodiments, CCD 26 may include a linear array of detectors (which may also be referred to as a one-dimensional array of detectors). In such cases, the linear array of detectors within CCD 26 is preferably oriented parallel to illumination line 18.

As described in more detail below, surface inspection apparatus 10 may be configured to scan surface 20 and, thus, may be configured to form illumination line 18 at different positions along surface 20. In such cases, the power and the integration time of the detector pixels may be fixed relative to each other. In other cases, however, CCD 26 may be configured to independently adjust an integration time of a set of detector pixels. An exemplary configuration of a surface inspection system having such an adjustment feature is described in U.S. Pat. No. 6,724,473 to Leong et al. In any case, illumination system 11 and collection system 21 may, in some embodiments, be stationary. Such a configuration may be advantageous for simplifying the optical alignment of apparatus 10, since there is substantially no relative motion between illumination system 11 and collection system 21. In such cases, surface 20 may, in some embodiments, be moved along a direction perpendicular to illumination line 18. In other cases, surface 20 may be rotated and, thus, scanned in a spiral path.

As shown in FIG. 1, lenses 22a and 22b and CCD 26 may be arranged in alignment about central optical axis 28. In general, collection system 21 is configured to have optical axis 28 oriented substantially normal to illumination line 18. In some embodiments, CCD 26 may also be arranged directly above illumination line 18. In other cases, CCD 26 may be oriented outside of the incidence plane of focused beam 16, such as in a double dark field configuration, to improve signal-to-noise ratio of defects. A double dark field collector configuration is referred to herein as a configuration in which the optical axis of the collector system is on a plane (defined by the collection optical axis and the surface normal) perpendicular to the incident plane of illumination and the detectors lie outside the incident plane. In some cases, collection system 21 may include a variable aperture to manipulate the numerical aperture of collection system 21. In some embodiments, collection system 21 may include a special shaped aperture to increase defect signal and reduce noise. In any case, it may be advantageous to image a central portion of illumination line 18 so that intensity variation along the image is insignificant. In some cases, a Fourier filter and/or a polarizer may be arranged between lenses 22a and 22b to gather relatively high signals from defects and relatively low signals from background surfaces.

In general, collection system 21 may be configured to project a magnified image of illumination line 18 onto CCD 26 so that each detector detects light from a corresponding portion of the illumination line. Such a process is denoted as block 62 in the flowchart illustrated in FIG. 5 and different embodiments of the process are described in more detail below in reference to FIGS. 6-8. In some embodiments, lens 22b may have a longer focal length than lens 22a such that a magnified image of illumination line 18 may be projected onto CCD 26. In such cases, collection system 12 serves as both an imager and a magnifier. In general, larger differences between the focal lengths of lenses 22a and 22b equate to larger degrees of magnification. In addition or alternative to lens 22b having a larger focal length than lens 22a, collection system 21 may, in some embodiments, include an optical magnifier for projecting a magnified image on to CCD 26.

In any case, collection system 21 may be configured to project a magnified image of illumination line 18 onto CCD 26 such that a width of the imaged illuminated line on the array of detectors is larger than the pixel size of the detectors along the x-direction (i.e., perpendicular to the illuminated line). The pixel size of the image may generally be governed by the size of the detector divided by the magnification of the collection system and further divided by the cosine (theta), where theta is the angle from surface normal to the optical axis of the collection system. A result of magnifying illumination line 18 to overfill detector pixels on CCD 26 is that the optical resolution of an image in the x-direction (as well as in the y-direction) will be dependent on the optical spot size of collection system 21 rather than the width of illumination line 18 and, thus, two dimensional imaging will occur. An exemplary case includes illumination system 11 generating an illumination line having a width of approximately 1 micrometer using a 266 nm wavelength laser source (current 266 nm wavelength illumination systems are generally restricted to forming illumination lines having dimensions approximately 1 micrometer or greater) and lens 22a having a numerical aperture of 0.65. In such an exemplary case, the optical spot size of collection system 21 in both the x and y directions will be approximately 0.5 micrometers. In this example, the 0.5 micrometer optical spot size in the x-direction is smaller than the 1 micrometer illumination line and, thus, two dimensional imaging will result.

Figure 6:
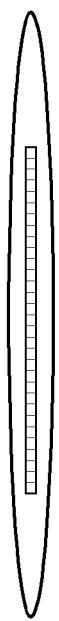
FIG. 6 depicts an exemplary image of an illuminated line including a linear array of pixels.
Figure 7:
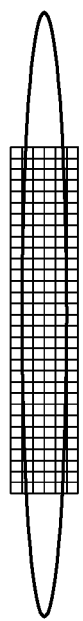
FIG. 7 depicts an exemplary image of an illuminated line including multiple columns of pixels extending beyond a boundary periphery of the illuminated image.
Figure 8:
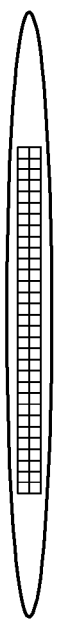
FIG. 8 depicts an exemplary image of an illuminated line including two columns of pixels.

Exemplary images of illuminated lines which have widths larger than pixel sizes of detectors are illustrated in FIGS. 6-8. More specifically, FIGS. 6-8 illustrate images of illuminated lines superimposed with detector pixels which are denoted by one or more columns of boxes. The distinction of the number of columns of pixels shown in each of the figures is explained in more detail below with respect to the different manners in which the imaging process may be performed. The boundaries of the magnified light are illustrated in FIGS. 6-8 by elliptically shaped lines. As shown in FIGS. 6-8, the widths of the detector pixels are smaller than the widths of the magnified illumination lines. It is noted that the elliptical shapes of the magnified light in FIGS. 6-8 are exemplary and the magnification of light in the surface inspection apparatuses described herein is not necessarily so limited. Furthermore, it is noted that the dimensions along the x-direction and the y-direction of each pixel may, in some case, be substantially the same as shown in FIGS. 6-8. In other embodiments, the x and y dimensions of the pixels may be different.

As noted above, the process of imaging a magnified portion of an illumination line onto an array of detectors may be performed in different manners. FIGS. 6-8 illustrate exemplary images of illuminated laser lines resulting from different techniques used for the imaging process. In particular, FIG. 6 illustrates exemplary image 64 of an illuminated laser line in which a magnified portion of the illuminated line is imaged using a single column of pixels on a CCD. Since only one pixel imaging is performed along the x-direction for the image depicted in FIG. 6, there is no focus variation of the image. Such a setup offers more practicality and simplicity than the two methods discussed below in reference to FIGS. 7 and 8. However, one pixel imaging along the x-direction may waste some laser power since only a portion of the laser intensity along x direction is used.

FIG. 7 illustrates exemplary image 66 of an illuminated laser line in which a magnified portion of the illuminated line is imaged using multiple columns of pixels. For such an image, a CCD using a time delay and integration (TDI) readout technique is used. In particular, the array of pixels depicted in FIG. 7 are imaged by shifting the surface being inspected along a direction of inspection and synchronizing a collection of photons from distinct regions of the surface. The different columns of pixels may correspond to different regions of the surface. As shown in FIG. 7, the multiple columns of pixels on TDI occupy the entire width of the imaged illumination line along the x-direction and, therefore, laser power is not wasted in such a process. Precautions, however, may be needed to insure focus uniformity of the image on side collectors which are tilted from the normal of the surface. Minimizing the width of an illumination line on a surface being inspected may minimize the focus variation of an image.

Another alternative manner in which to image a surface is described in reference to FIG. 8. In particular, FIG. 8 illustrates exemplary image 68 of an illuminated laser line in which a magnified portion of the illuminated line is imaged using only two columns of pixels. Taken more broadly, an alternative technique for imaging a surface may include only imaging a number of pixel columns which may fit within an area of a magnified portion of an illuminated laser line. Such a process may be imaged by a CCD using a time delay and integration (TDI) readout technique. In general, the technique of imaging a surface to a number of pixel columns which may fit within an area of a magnified portion of an illuminated laser line may offer a compromise to the conflicting consequences of the techniques described in reference to FIGS. 6 and 7. In particular, the technique of imaging a surface to a number of pixel columns which may fit within an area of a magnified portion of an illuminated laser line may offer a manner in which to optimize the use of laser power within the system. Imaging a portion of illumination width may reduce focus uniformity of the image.

Figure 9A:
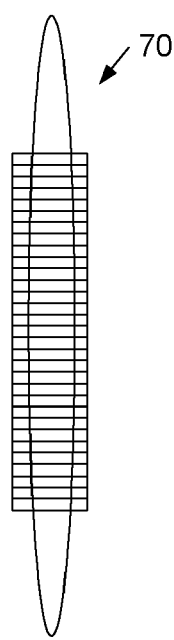
FIG. 9a depicts an exemplary image of an illuminated line including a linear array of rectangular-shaped pixels.
Figure 9B:
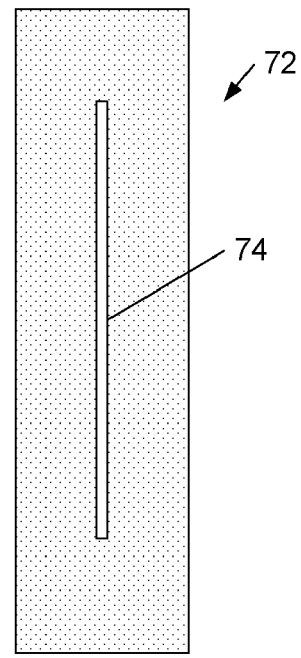
FIG. 9b depicts a plan view of an exemplary plate having a relatively narrow slit.
Figure 9C:
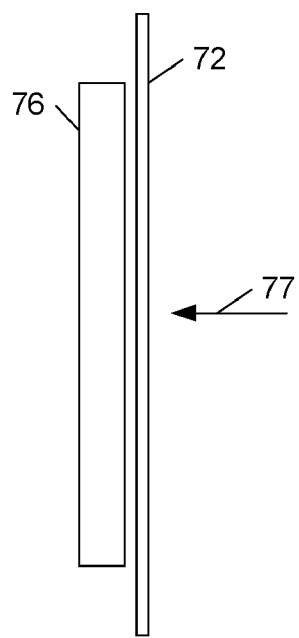
FIG. 9c depicts an exemplary side view of the plate depicted in FIG. 9b arranged in proximity to an array of detectors of an imaging system.
Figure 9D:
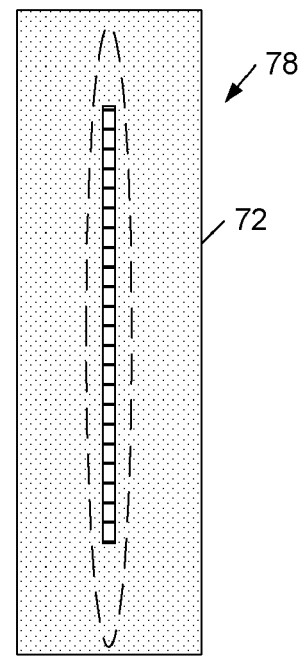
FIG. 9d depicts an exemplary image of an illuminated line including a linear array of pixels formed using the arrangement of imaging system components depicted in FIG. 9c.

Another way to image an illumination line onto an array of detectors such that a width of the imaged illuminated line on the array of detectors is larger than the pixel size of the detectors along the x-direction (i.e., perpendicular to the illuminated line) is to limit light gathered onto the detectors. FIGS. 9a and 9b illustrate an exemplary manner in which a single column of pixels on a CCD images an illuminated line similar to the depiction shown in FIG. 6. FIG. 9a illustrates exemplary image 70 of an illuminated laser line in which a portion of the illuminated line is imaged using a single column of pixels on a CCD. As shown in FIG. 9a, the rectangular-shaped pixels on the detectors are wider along the x-direction than the width of the imaged illuminated line on the array of detectors and, consequently, one dimensional imaging is formed. It is noted that the dimensions along the x-direction and the y-direction of each pixel may or may not be same. To alternatively facilitate image pixel sizes narrower than the width of the non-magnified imaged illuminated line, the collection system may be configured to limit light gathered onto the detectors as described below in reference to FIGS. 9b-9d.

FIG. 9b illustrates plate 72 having exemplary slit 74 oriented parallel to the illumination line for passing light onto an array of detectors. In particular, as shown in the side view of FIG. 9c, plate 72 may be arranged adjacent to CCD 76 to limit light 77 from the focusing lens of the collection system passing there through. The elongated direction of slit 74 is parallel to the elongated dimension of illumination line (i.e., the elongated direction of slit 74 is arranged along the y-direction). As a result of placing plate 72 in front of CCD 76, the pixel size of the detectors along the x-direction may be narrower than the width of the imaged illuminated line on the array of detectors as shown by image 78 depicted in FIG. 9d. (The imaged illumination line is depicted by dotted lines to emphasize the CCD is behind plate 72.)

Such an imaging process may be referred to as one dimensional confocal imaging. In this imaging mode, the optical resolution size in the x-direction is dependent on the width of slit 74 and the optical resolution in the y-direction is dependent on optical size of the collection system. An advantage of this one dimensional confocal imaging process is that it concentrates on regions of the surface being inspected and rejects previous region noises. To accommodate the one dimensional confocal imaging process described in reference to FIGS. 9a-9d, surface inspection systems may include an alternative configuration of a collection system than described for collection system 21 of FIG. 1. In particular, a surface inspection system may include a plate with a slit to limit the transmission of light from the imaging and focusing lenses to the array of detectors, such as the plate described in reference to FIG. 9b. The slit width may be variable in such cases.

Figure 2:
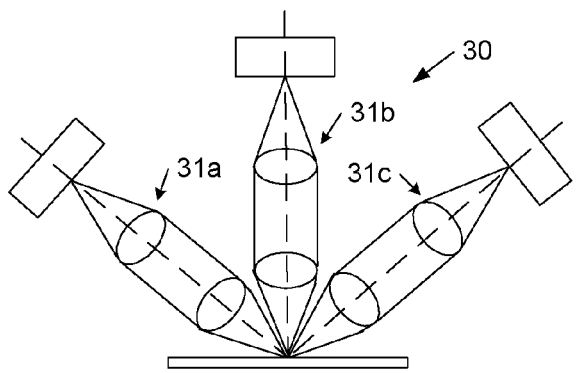
FIG. 2 depicts a partial cross-sectional view of an alternative surface inspection system.
Figure 3:
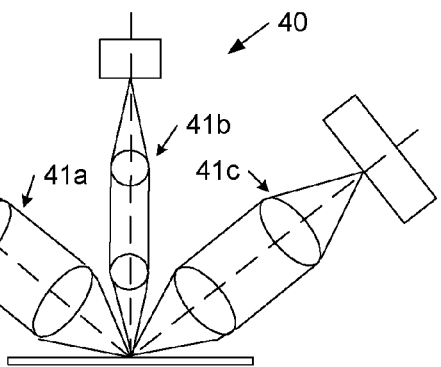
FIG. 3 depicts a partial cross-sectional view of yet another surface inspection system.
Figure 4:
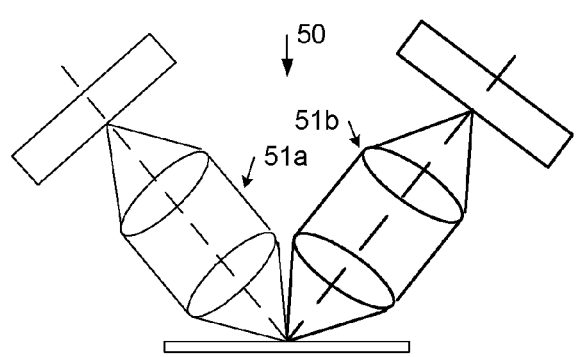
FIG. 4 depicts a partial cross-sectional view of yet another alternative surface inspection system.
Figure 5:
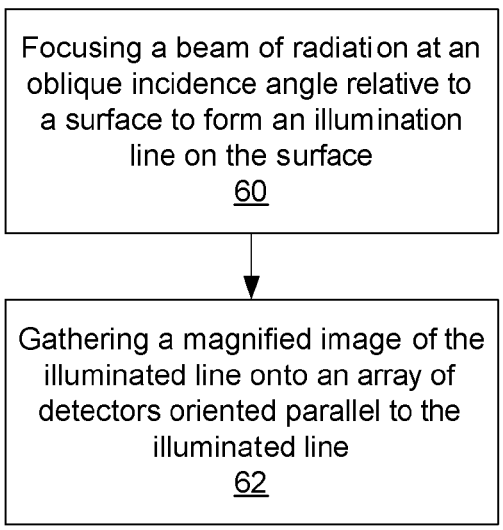
FIG. 5 depicts a flowchart of a method for imaging an illuminated line on a surface using any one of the surface inspection systems illustrated in FIGS. 1-4.

In some cases, the surface inspection apparatuses described herein may include a plurality of collection systems, such as depicted for surface inspection apparatuses 30, 40, and 50 in FIGS. 2-4, respectively. As noted above, FIGS. 2-4 illustrate partial cross-sectional views of surface inspection apparatuses 30, 40, and 50 having alternative configurations of collections systems as compared to apparatus 10. In particular, FIGS. 2-4 illustrate surface inspection apparatuses 30, 40, and 50 each having a different configuration of multiple collections systems oriented at different directions relative to the incidence plane. The illumination systems of each of the apparatuses are not shown in FIGS. 2-4 to simplify the drawings. In particular, surface inspection apparatuses 30, 40, and 50 are illustrated to emphasize some exemplary arrangements of collections systems which may be employed within the apparatuses described herein and, therefore, do not illustrate all components of the apparatuses such an illumination systems.

In general, the optical spot size of the two-dimensional imaging systems described herein depends on the number of collection systems used in the systems. It is noted that the number and arrangement of collection systems depicted in FIGS. 2-4 do not limit the possible configurations for the surface inspection apparatuses described herein. In particular, the surface inspection apparatuses described herein may include any number and any arrangement of collection systems, depending on the design specifications of the individual apparatuses. In general, the collection systems depicted in surface inspection apparatuses 30, 40, and 50 may include similar components as those described for collection system 21 of FIG. 1, with exceptions of size (i.e., slit) and/or orientation. As such, for the sake of brevity, the description of the components for collection system 21 is referenced for the collection systems of surface inspection apparatuses 30, 40, and 50.

As shown in FIG. 2, collection systems 31a, 31b and 31c of surface inspection apparatus 30 may be of substantially equal size (i.e., aperture) and configuration with exception to their orientation relative to each other. It is noted that all three collection systems are on planes perpendicular to the illumination plane. In some embodiments, collection systems 31a, 31b, and 31c may be equally spaced from each other as shown in FIG. 2. In other embodiments, the spacing between collection systems 31a, 31b, and 31c may not be uniform. In either case, a setup of equally sized collection systems within a surface inspection apparatus may be used for a variety of configurations, but may be particularly suitable for embodiments in which the maximum numerical aperture for each collector is used. In cases in which a 266 nm laser and a maximum numerical aperture of 0.5 is used in surface inspection apparatus 30, the optical spot size of the system along the x-direction may be approximately 0.65 micrometers. Larger or smaller apertures and/or optical spot size dimensions, however, may be possible. In particular, depending on the space needed for illumination optics and the space needed for collection optic housing, these numbers will vary.

In some embodiments, the surface inspection apparatuses described herein may include a collection system of a different size than other collection systems in the apparatus. Illustrating such an alternative configuration, FIG. 3 depicts surface inspection apparatus 40 including side collection systems 41a and 41c which are of substantially the same size and bigger than center collection system 41b. Although the configuration of having smaller collection system 41b interposed between larger collection systems 41a and 41c may be advantageous for inspecting some surfaces, the arrangement of the collection systems are not necessarily so limited.

Another exemplary configuration of a surface inspection system having multiple collection systems is illustrated in FIG. 4. In particular, FIG. 4 illustrates surface inspection apparatus 50 including two collection systems 51a and 51b which are of substantially the same size and are oriented at approximately the same angle relative to surface 20. The use of two relatively large collectors (versus using three collectors as described in reference to FIGS. 2 and 3) may be used for a variety of configurations, but may be particularly suitable for inducing a minimum optical spot size for the system, particularly smaller than the illumination line imaged by the system. The maximum possible numerical aperture for such a setup is approximately 0.71. In cases in which a 266 nm laser is used in surface inspection apparatus 50, the minimum optical spot size dimension of an image of an illumination line along the x-direction may approximately 0.46 micrometers. Larger or smaller apertures and/or optical spot size dimensions, however, may be possible.

The apparatuses described herein may be compact, may have a simple architecture, and may provide a relatively low cost alternative for inspecting patterned wafers. Due to the low cost of the apparatuses, it may, in some embodiments, be advantageous use one in conjunction with another surface inspection apparatus for inspecting two different surfaces of an object. Thus, a system may include a front side inspection apparatus (similar to those described herein) for inspecting the front side of a surface and another system (which may or may not be similar to those described herein) for inspecting the backside of the surface or vice versa. If, as in the apparatuses described above, the illumination and collection systems of the apparatuses remain stationary and the surface is inspected by moving the surface, the two apparatuses may need to be synchronized.

It is noted that the shapes of collectors, specifically the lenses of collection system 21 described above in reference to FIGS. 1-9d are circular. Circular shaped collectors have equal optical spot sizes in both the x and y directions. Collectors of other shapes are possible. For example, elliptical shaped collectors with a long axis parallel to the y direction have a larger collection aperture in the y-direction than in the x direction. Therefore, optical spot size in y direction will be smaller than that in the x direction in such cases.

It will be appreciated by those skilled in the art having the benefit of this disclosure that this invention is believed to provide surface inspection apparatuses and associated methods configured to image an illuminated line of a surface based upon two dimensional imaging. Further modifications and alternative embodiments of various aspects of the invention will be apparent to those skilled in the art in view of this description. For example, although the apparatuses and methods described herein are specifically described for the inspection of semiconductor wafers, they are not necessarily so limited. In addition, although the methods described herein utilize oblique illumination, the methods may alternatively use normal illumination. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A surface inspection apparatus, comprising:
    an illumination system configured to focus a beam of radiation at a non-orthogonal incidence angle relative to a surface to form an illumination line on the surface substantially in a plane of incidence of the focused beam, wherein the plane of incidence is defined by the focused beam and a direction that is through the focused beam and normal to the surface; and
    a collection system configured to image the illumination line, wherein the collection system comprises:
        an imaging lens for collecting light scattered from a region of the surface comprising the illumination line;
        a focusing lens for focusing the collected light; and
        a device comprising an array of light sensitive elements, wherein each light sensitive element of the array of light sensitive elements is configured to detect a corresponding portion of a magnified image of the illumination line, and wherein the collection system is configured to image the illumination line in a manner such that the width of the imaged illumination line on the array of detectors is larger than the pixel size of the detectors along the same direction.

2. The surface inspection apparatus of claim 1, wherein a column of the light sensitive elements on the device is oriented parallel to the illumination line, and wherein the collection system is configured to magnify the image focused by the focusing lens such that the width of the imaged illumination line on the array of detectors is larger than the pixel size of the detectors along the same direction.

3. The surface inspection apparatus of claim 1, wherein a column of the light sensitive elements on the device is oriented parallel to the illumination line, wherein the collection system further comprises a plate interposed between the focusing lens and the device, and wherein the plate comprises a slit oriented parallel to the illumination line to limit the light gathered by the device such that the pixel size of the detectors perpendicular to the illumination line is narrower than the width of the imaged illumination line.

4. The surface inspection apparatus of claim 1, wherein the device is configured to perform time delay and integration (TDI) techniques.

5. The surface inspection apparatus of claim 4, wherein the device is configured to image the illumination line using multiple columns of pixels with the TDI techniques.

6. The surface inspection apparatus of claim 1, wherein the device is configured to image the illumination line using a single column of pixels.

7. The surface inspection apparatus of claim 1, wherein the device is configured to independently adjust an integration time of a set of light sensitive elements.

8. The surface inspection apparatus of claim 1, wherein the surface comprises a semiconductor wafer, and wherein the surface inspection apparatus further comprises a support structure for the semiconductor wafer.

9. The surface inspection apparatus of claim 1, wherein the collection system is one of a plurality of collections systems.

10. The surface inspection apparatus of claim 9, wherein each of the plurality of collection systems comprise a maximum numerical aperture relative to their given size.

11. The surface inspection apparatus of claim 1, wherein at least one of the focusing lens and the imaging lens is circular.

12. The surface inspection apparatus of claim 1, wherein at least one of the focusing lens and the imaging lens is elliptical.

13. A method for inspecting a surface, comprising:
    focusing a beam of radiation at a non-orthogonal incidence angle relative to a surface to form an illumination line on the surface, wherein the illumination line is substantially in a plane of incidence of the focused beam defined by the focused beam and a direction that is surface normal; and imaging the illumination line onto an array of detectors oriented parallel to the illumination line such that the width of the imaged illumination line on the array of detectors is larger than the pixel size of the detectors along the same direction.

14. The method of claim 13, wherein the step of imaging the illumination line comprises magnifying an image from the illumination line.

15. The method of claim 13, wherein the step of imaging the illumination line comprises limiting transmission of the light from the illumination line to the array of detectors.

16. The method of claim 13, wherein the step of imaging the illumination line comprises:

shifting the surface along a direction of inspection; and synchronizing a collection of photons from distinct regions of the surface.

17. The method of claim 13, wherein the step of imaging the illumination line comprises adjusting an integration time of a set of the detectors.

18. The method of claim 13, wherein the step of focusing the beam of radiation comprises forming the illumination line having a minimum width configurable by the system used to focus the beam of radiation.

19. The method of claim 13, wherein the step of focusing the beam of radiation comprises forming the illumination line upon a semiconductor wafer surface.

* * * * *